United States Patent [19]

Ryan

[11] Patent Number: 4,925,692
[45] Date of Patent: May 15, 1990

[54] FOOD COMPOSITION CONTAINING A SILOXANE POLYMER AND A PARTICULATE SILICA

[75] Inventor: John W. Ryan, Midland, Mich.

[73] Assignee: Dow Corning Corporation, Midland, Mich.

[21] Appl. No.: 267,949

[22] Filed: Nov. 7, 1988

[51] Int. Cl.$^5$ .............................................. A23L 1/307
[52] U.S. Cl. .................................... 426/531; 426/601; 426/84
[58] Field of Search ...................... 426/531, 601, 804

[56]  References Cited

U.S. PATENT DOCUMENTS 3,600,186  8/1971  Mattson et al. .
3,954,976  5/1976  Mattson et al. .
4,005,196  1/1977  Jandacek et al. .
4,034,083  7/1977  Mattson et al. .
4,461,782  7/1984  Robbins et al. .

OTHER PUBLICATIONS

European Patent Application 0 205 273, published 12/17/86, Dow Corning Corporation, 64 pages.

Primary Examiner—Joseph Golian
Attorney, Agent, or Firm—James E. Bittell

[57]  ABSTRACT

What is disclosed are food compositions which contain a polyorganosiloxane fluid as a fat substitute and an anti-anal leakage agent. The anti-anal leakage agents comprise $C^{12}$–$C_{24}$ essentially saturated fatty acids or edible, digestible sources thereof; non-degradable, water insoluble fibers of plant origin; and silica.

12 Claims, No Drawings

FOOD COMPOSITION CONTAINING A SILOXANE POLYMER AND A PARTICULATE SILICA

BACKGROUND OF THE INVENTION

Certain edible, but non-absorbable and non-digestible, polyorganosiloxane fluids can be used as low calorie fat substitutes in foods and in food processing. The present invention relates to methods for the reduction of potential anal leakage of polyorganosiloxane fluids when used in the aforementioned applications.

Fat constitutes about 40 percent of the total calories in the human diet. Furthermore, fat is the most concentrated form of energy in the diet, with each gram of fat supplying approximately nine calories. Typical sources of fats in the diet are in such products as margarine, mayonnaise, salad oils, baked goods and deep fried foods. Dietary fat has been causally associated with a significant number of disease states of humans.

One of the most common metabolic problems among people in developed countries today is obesity. Obese individuals are at a higher risk for coronary complications such as heart attacks and angina as well as manifestation of symptoms of diabetes. In addition many people attempt to restrict caloric intake for reasons of personal appearance. In some societies the obese person is discriminated against as to employment opportunities and social organization memberships.

An Executive Summary prepared by the Committee on Diet, Nutrition and Cancer, National Academy of Sciences, National Academy Press, Washington, D.C., p. 4–5 (1982), discusses a possible link between cancer and the intake of fat. Epidemiological studies have shown an association between dietary fat and the occurrence of cancer at several sites, especially the breast, prostate and large bowel. In addition numerous studies in animals have shown that dietary fats influence tumorigenesis, especially in the breast and the colon.

The National Institutes of Health Consensus Development Conference published "Lowering Blood Cholesterol to Prevent Heart Disease", in JAMA, Vol. 253, No. 14, p. 2080-2086 (1985). The authors concluded that elevation of blood cholesterol levels is a major cause of coronary artery disease, and that lowering elevated blood cholesterol levels will reduce the risk of heart attacks caused by coronary disease. The Panel recommended appropriate changes in the diet, particularly a reduction in the amount of fat eaten, in order to reduce blood serum cholesterol levels.

These studies demonstrate the desirability of methods to reduce the amount of fat in the diet, in order to reduce the risk and social cost associated with obesity, cancer, and heart disease.

Desirable features for a fat replacement in foods are: (1) resistance to digestion by the body; (2) non-absorption through oral and gastrointestinal mucosa into body when consumed; (3) minimal toxicity; (4) thermal stability for cooking uses; (5) functional and physical properties comparable to or superior to natural fats and oils such as lending texture to cakes, enhancing flavors, and enhancing taste; (6) reasonably priced.

The polyorganosiloxane fluids of this invention incorporate many of the desirable feature for a fat replacement and their use in such a capacity may be beneficial in reducing health related risk and problems associated with high fat diets. Numerous studies in various animal species (rats, mice, rabbits, dogs and monkeys) have established the safety and lack of toxicity of polydimethylsiloxanes and related organosilicones. Studies with C-14 labeled materials have shown that adequately devolatilized silicone polymers are not absorbed from the gastrointestinal tract, and that such materials are eliminated in the fecal contents.

Because of their safety and other inherent properties polydimethylsiloxanes have been widely used at the part per million (ppm) level for applications involving food processing and food contact. These applications, have included release coatings, defoaming agents, and anti-oxidant agents among other applications.

A book written by Weiss, T. J., *Food Oils and Their Uses*, (AVI Publishing Co., Inc., Westport Conn., 1983, p. 112) reviews articles suggesting various ppm uses for silicones in association with food. Under the section entitled "Antifoam Agents", Weiss disclosed that Babyan had shown that the presence of small amounts (ppm) of silicone oil in deep frying oil increased the smoke point of the oil by about 14° C. (25° F.) and that silicones (in 0.5 to 3 ppm quantities) when added to frying fats inhibit foam formation. It was further suggested in the reviewed articles that larger quantities of silicone oils (50–100 ppm) may even cause foaming of the frying fat where it is not ordinarily expected. The suggestion is also presented that the silicone antifoams may be deleterious in cakes, in frying doughnuts and in manufacturing potato chips, all in an antifoaming, i.e. ppm, context.

Certain other non-silicone low calorie fat substitutes have been disclosed in the prior art in U.S. Pat. No. 3,600,186, issued Aug. 17, 1971 to Mattson, et al.; U.S. Pat. No. 3,954,976, issued May 4, 1976 to Mattson, et al.; U.S. Pat. No. 4,005,196, issued Jan. 25, 1977 to Jandacek, et al.; U.S. Pat. No. 4,034,083, issued July 5, 1977 to Mattson; and U.S. Pat. No. 4,461,782 issued July 24, 1984 to Robbins, et al.

Ingestion of moderate to high levels of non-degradable oily substances which are liquid at body temperature produce an undesirable leakage of the oily material through the anal sphincter. This leakage is commonly referred to as anal leakage. The consequence of this leakage can be the soiling of clothing, with subsequent soiling of seating apparatus and assoicated embarrassment.

Jandacek, U.S. Pat. No. 4,005,195 discloses anti-anal leakage (AAL) agents for use with liquid polyester materials. These anti-anal leakage agents include solid fatty acids (melting point 37° C. or higher) and their triglyceride source, and solid polyol fatty acid polyesters. Specifically, the agents are selected from the group consisting of: edible $C_{12}$ and higher saturated fatty acids, and their edible salts; edible, digestible sources of $C_{12}$ and higher fatty acids; edible; nonabsorbable, nondigestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, nondigestible esters of alpha-branched chain $C_{10}$–$C_{18}$ fatty acids.

The present invention relates to a method of controlling the anal leakage of polyorganosiloxane fluids used as fat substitutes in food by adding an anti-anal leakage agent of the type disclosed hereinafter to the liquid siloxane or to foods containing same.

SUMMARY OF THE INVENTION

Non-degradable polyorganosiloxane fluids can be substituted for fats in food compositions. However, rats fed a diet containing about 6.5% by weight of polyorganosiloxane fluid exhibited undesirable anal leakage of the siloxane fluid. It has now been determined that this undesirable affect can be obviated by combining the polyorganosiloxane fluid with certain anti-anal leakage (AAL) agents. The types of AAL agents which can be used to overcome the above-described anal leakage problem are disclosed herein.

For purposes of this invention, the silicones can be described as polyorganosiloxanes which have an organic carbon content of at least fifteen (15) weight percent. Included within the scope of this invention are those siloxanes having organic substitutions wherein the organic substitution is linked to the silicon atom through a carbon/silicon bond. Such a limitation distinguishes the siloxanes useful in this invention from those wherein there is no organic substitution such as partial hydrolyzates and condensates of $Si(OR)_4$ wherein R is an alkyl radical. Further, this invention contemplates small amounts of —Si—O—C— bonded materials wherein the hydrolyzable by-products of such materials are not toxic to the human body, such as for example, ethanol, glycerol, sucrose and other organic sugars.

In order to minimize the possibility of absorption of the siloxanes in the gastrointestinal tract, the siloxanes preferred for this invention should not contain significant amounts of material with molecular weights of less than 500 g/mole. By "significant", it is meant that there should be less than about 10 weight percent of such low molecular weights materials present in the composition, based on the total siloxane present. Preferred for this invention are siloxanes that are essentially free of low molecular weight materials as defined.

Also, preferred for this invention is a polyorganosiloxane fluid of the general formula $(CH_3)_3Si-O[(CH_3)_2SiO]_bSi(CH_3)_3$ wherein b has an average value of 25 to 500.

The siloxanes of this invention need not necessarily be truly soluble or miscible with the other components of the foods in which they are being used. They may be combined with the food either separately or in combination with the anti-anal leakage agent.

The polyorganosiloxane fluid may be substituted in the food in a quantity of about 0.1 to 100 percent of the total food composition. The amount of siloxane used will depend on the amount of fat in the food composition.

Types of food compositions within the scope of this invention include salad oils, and salad dressings; dairy products such as cheese, cottage cheese, milk, ice cream, whipped cream and yogurt; baked goods such as cakes, pie crusts, cookies, bread, cereal, doughnuts and crackers; shortening substitutes; margarine; mayonnaise; peanut butter; and other food compositions where the fat component can be substituted with silicone oil.

One class of materials which provide the AAL effect herein includes fatty acids having a melting point of ca. 37° C. or higher, and ingestible, digestible sources of such fatty acids. The fatty acid AAL agents include, for example, the $C_{12}$–$C_{24}$ saturated fatty acids, and ingestible, digestible sources thereof.

Non-limiting examples of saturated fatty acids and sources thereof which can be used as the AAL agent herein include the free saturated fatty acids per se, compounds such as esters (e.g. triglycerides) that yield such saturated fatty acids on hydrolysis in the gut, soaps of the fatty acids such as the sodium, potassium, water-soluble soaps, as well as the calcium and magnesium water-soluble soaps.

Highly preferred herein for their anti-anal leakage effect are the $C_{16}$–$C_{22}$, most preferably $C_{16}$–$C_{18}$, saturated fatty acids, or edible sources thereof.

Specific examples of materials useful as the foregoing type of AAL agent herein include $C_{16}$–$C_{22}$ saturated fatty acids such as stearic acid, natural or processed fats yielding $C_{12}$–$C_{24}$ saturated fatty acids in the gut, e.g. materials such as cocoa butter, palm oil, palm kernel oil, coconut oil, tallow, lard, suet, enriched concentrates of triglycerides having high levels of saturated fatty acids obtainable from these sources and sources such as highly saturated cottonseed oil fractions obtained by processes such as crystallization or directed rearrangement which yield the desired higher concentrations of the more saturated fatty acids in the resulting "hardstock" fractions.

Partially hydrogenated oils including all of the above, as well as partially hydrogenated soybean oil, safflower seed oil, rapeseed oil, or such materials which are hydrogenated and concentrated, for example by crystallization, to provide fractions which are enriched in sources of the longer chain, substantially saturated fatty acids, are all useful as the AAL agent herein. (By "substantially hydrogenated" herein is meant oils having an iodine value of ca. 50, or lower.) Any of the foregoing unsaturated oils are useful herein after they have been substantially completely hydrogenated to convert the unsaturated fatty acid (ester) groups to the corresponding saturated fatty acids.

A second class of materials which provided the anti-anal leakage effect described herein is particulate silica. To be effective at the concentrations claimed herein the particulate silica should have a surface area of greater than 10 $m^2/g$ as determined by the BET method. The BET method of measuring surface area is based on the adsorption of nitrogen at its boiling point under 1 atm pressure and measures both the interior as well as the total surface area of the particles. For the present invention it is believed that the exterior surface area of the particle is the critical area. In cases where particles have considerable surface area interior to the particle, it is anticipated one skilled in the art will appropriately adjust the weight of silica used to provide the requisite exterior surface area.

Preferred is a silica with a surface area of at least 80 $m^2/g$ and most preferred is a silica with a surface are of about 300 $m^2/g$ to about 400 $m^2/g$.

The silica particles used as the AAL agent may be produced by any process adequate to produce the required surface area including grinding, milling, precipitation and vapor phase deposition.

A third class of materials which provided the anti-anal leakage effect described herein is edible, non-degradable, water insoluble fibers of plant origin. By edible is meant those fibers which are palatable or can be rendered palatable by treatment or appropriate formulation. In addition edibility implies the fibers, associated constituents, and degradation products thereof are to be essentially non-toxic when ingested at the levels contemplated in this invention. Non-degradable refers to the ability to pass through the gastrointestinal tract essentially unchanged by normal digestive and bacterial processes. Water insoluble fibers of plant origin includes those fibers comprising cellulose, hemicellulose, and lignin in combination or isolates thereof.

A preferred embodiment of this class of anti-anal leakage agents is bran. Bran is a natural source of fiber consisting essentially of the water insoluble coats of seeds of legumes and cereals. Legumes refer to the seeds and fruits of dicotyledonous plants such as beans, peas, clover and alfalfa. Cereal relates to a plant yielding farinaceous grain suitable for food such as corn, wheat, oat, rye, barley, and rice. Farinaceous refers to grains rich in starch.

Also, included within the scope of this invention are isolates comprising cellulose, hemicellulose, and lignin separately or in combination. Fiber from plant sources other than those specified are also useful as anti-anal leakage agents.

Preferred AAL agents of this invention include cellulose, hemicellulose, and lignin fibers or sources thereof with an average mean particle size of less than about 36 microns. Such AAL agents with an average mean particle size of less than about 28 microns are more preferred. Another preferred AAL agent of this invention is the bran flour of cereal grains which 100% passes a USS 40 mesh screen and 90% is retained by a USS 120 mesh screen.

The AAL agent may be incorporated into the food composition either separately or by first being combined with the siloxane fluid. The AAL agent and fluid in combination or individually may be added to the food as appropriate during formulation, processing, or preparation. It is preferred that the AAL agent be present in the final food composition at a concentration of at least about 10% by weight of the combined siloxane and AAL agent portions of the food composition. It is more preferred that the AAL agent be present in the final food composition at a concentration of at least about 20% be weight of the combined siloxane and AAL agent portions of the food composition. It is most preferred that the AAL agent is present at a concentration of about 20% to about 50% by weight of the combined siloxane and AAL agent portions of the food composition. These concentrations as specified reduce or abolish anal leakage of the siloxane fluid.

Those skilled in the art will recognize that the disclosed AAL agents if found normally in a food may allow adjustment of the actual AAL agent required to be added to the food. In addition, it may be recognized that diets containing the disclosed AAL agents could reduce the amount of AAL agent needed in a food composition to prevent anal leakage. The concentrations presented in the food compositions of this invention are those which reduce or prevent anal-leakage in the absence of other potential sources of AAL agent activity.

The following non-limiting examples illustrate the composition of this invention.

EXAMPLE 1

As a control food composition a polyorganosiloxane fluid of the general formula $(CH_3)_3SiO[(CH_3)_2SiO]_b$-$Si(CH_3)_3$ wherein b had an average value of about 35 was blended into Purina Rat Chow 5012 Meal (Ralston Purina Company, ST. Louis, Missouri) in the proportions of: 1500 g rat chow + 105 g siloxane fluid. A group of five adult rats weighing 275-350 g was allowed ad libitum access to this food composition as their exclusive diet for seven days. Animals were observed daily for evidence of anal leakage. Within 48 hours of access to this diet all animals demonstrated slight to moderate anal leakage of the siloxane fluid.

EXAMPLE 2

Stearic acid, as representative of the group of $C_{12}$-$C_{24}$ saturated fatty acids, was incorporated as an AAL agent into the food composition of Example 1 in the following proportions: 1500 g rat show +105 g siloxane fluid+30 g stearic acid. Other experimental details were the same as those specified in Example 1. None of the five animals fed this diet with stearic acid added as an AAL agent demonstrated signs of anal leakage of the siloxane fluid at any time during the seven day observation period.

EXAMPLE 3

Suet is representative of naturally occurring digestible fats which can serve as a source for $C_{12}$-$C_{24}$ saturated fatty acids and their esters. In this example the food composition of Example 1 was blended with suet as an AAL agent in the following proportions: 1500 g rat chow+105 g siloxane fluid+30 g suet. Other experimental details where the same as in Example 1. None of the five animals fed this diet with suet added as an AAL agent demonstrated signs of anal leakage of the siloxane fluid at any time during the seven day observation period.

EXAMPLE 4

To the food composition of Example 1 was added silica with an average surface area of about 300 m$^2$/g to about 400 m$^2$/g in the proportions of 1500 g rat chow+105 g siloxane fluid+"n" g silica wherein n was 1, 3, 7, 15, or 30 g. Other experimental details where the same as in Example 1. A separate group of five animals each was used for each food composition tested. All test groups displayed a reduction in the incidence and severity of anal leakage in relation to the control group of Example 1. In general, as more silica was added to the diet the time to appearance of anal leakage increased and the number of animals displaying anal leakage decreased. Only the test group receiving the diet containing 30 g of silica was free of all signs of anal leakage of siloxane fluid.

EXAMPLE 5

To the food composition of Example 1 was added silica with a particle size of 32-63 micrometer in the proportions of: 1500 g rat chow+105 g siloxane fluid+30 g silica. Other experimental details were the same as given in Example 1. Silica of this particle size at the concentration tested effected a reduction in the severity and incidence of anal leakage of siloxane fluid in relation to the control group of Example 1. However, complete abatement of the anal leakage in all animals of the test group was not achieved.

EXAMPLE 6

Solka Floc 200 (James River Corporation, Hackensack, NJ) a mechanically ground cellulose of 30-35 micrometer average particle size was added to the food composition of Example 1 in the following proportion: 1500 g rat chow+105 g siloxane fluid+30 g of Solka Floc 200. Other experimental details were the same as given in Example 1. Solka Floc 200 at the concentration tested reduced the severity and incidence of anal leakage of siloxane in relation to the control group of Example 1. However, complete abatement of anal leakage in all animals of the test group was not achieved.

EXAMPLE 7

Solka Floc 300 (James River Corporation, Hackensack, NJ) a mechanically ground cellulose of 22-24 micrometer average particle size was added to the food composition of Example 1 in the following proportions: 1500 g rat chow + 105 g siloxane fluid + 30 g of Solka Floc 300. Other experimental details were the same as those of Example 1. One of five test animals had signs of slight anal leakage of the siloxane fluid at 24 and 48 hours after being placed on the test diet containing Solk Floc 300. At 72 hours after being placed on the test diet and thereafter, none of the test animals had signs of anal leakage.

EXAMPLE 8

Barley bran, a natural source of plant fibers, was added to the food composition of Example 1 in the following proportion: 1500 g rat chow + 105 g siloxane fluid + 30 g barley bran. The barley bran was purchased from National Grain Products Co., Inc., Minnetonka, MN. The bran was produced from barley after malting and removal of sugar and starch by hot water extraction. The extracted barley was dried by indirect steam, milled and sifted to obtain flour which 100% passed through a USS 40 mesh screen and 90% was retained by a USS 120 mesh screen. Other experimental details were the same as those of Example 1. None of the test animals exhibited signs of anal leakage of the siloxane fluid at any time during the test period.

What is claimed is:

1. A low calorie food composition comprising non-fat ingredients and fat ingredients wherein about 0.1% by weight to about 100% by weight of the total fat ingredients have been replaced by a fat substitute comprising:
   (a) an edible, non-absorbable, non-digestible liquid siloxane polymer of the general formula $(CH_3)_3SiO((CH_3)_2SiO)_bSi(CH_3)_3$ wherein b has an average value of 25 to 500; and
   (b) sufficient particulate silica to prevent leakage of said liquid siloxane through the anal sphincter.

2. A composition according to claim 1 wherein the liquid siloxane comprises at least about 10% by weight of particulate silica.

3. A composition according to claim 1 wherein the liquid siloxane comprises at least about 20% by weight of particulate silica.

4. A composition according to claim 1 wherein the liquid siloxane comprises at least about 10% to about 50% by weight of particulate silica.

5. A composition according to claim 1 wherein the liquid siloxane comprises from about 20% to about 50% by weight of particulate silica.

6. A composition according to claim 5 wherein the anti-anal leakage agent comprises a particulate silica with surface area of about 10 m$^2$/g to about 500 m$^2$/g.

7. A composition according to claim 6 wherein the anti-anal leakage agent comprises a particulate silica with surface area of about 80 m$^2$/g to about 500 m$^2$/g.

8. A composition according to claim 7 wherein the anti-anal leakage agent comprises a particulate silica with surface area of about 300 m$^2$/g to about 400 m$^2$/g.

9. A method for reducing the anal leakage of an edible, non-absorbable, non-digestible liquid siloxane polymer of the general formula

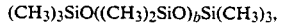

$(CH_3)_3SiO((CH_3)_2SiO)_bSi(CH_3)_3$, wherein b has an average value of 25 to 500, when the liquid siloxane is used as a fat substitute in food compositions to reduce the caloric content of the food composition, comprising:
   (a) replacing about 0.1% by weight to about 100% by weight of total fat ingredients of the food composition with the liquid siloxane, creating a reduced calorie food composition;
   (b) adding sufficient particulate silica to the reduced calorie food composition to prevent anal leakage of the liquid siloxane when the reduced calorie food composition is ingested.

10. A method according to claim 9 wherein the anti-anal leakage agent comprises a particulate silica with surface area of about 10 m$^2$/g to about 500 m$^2$/g.

11. A method according to claim 10 wherein the anti-anal leakage agent comprises a particulate silica with surface area of about 80 m$^2$/g to about 500 m$^2$/g.

12. A method according to claim 11 wherein the anti-anal leakage agent comprises a particulate silica with surface area of about 300 m$^2$/g to about 400 m$^2$/g.

* * * * *